MINIATURE ROSE PLANT
Filed Aug. 18, 1975
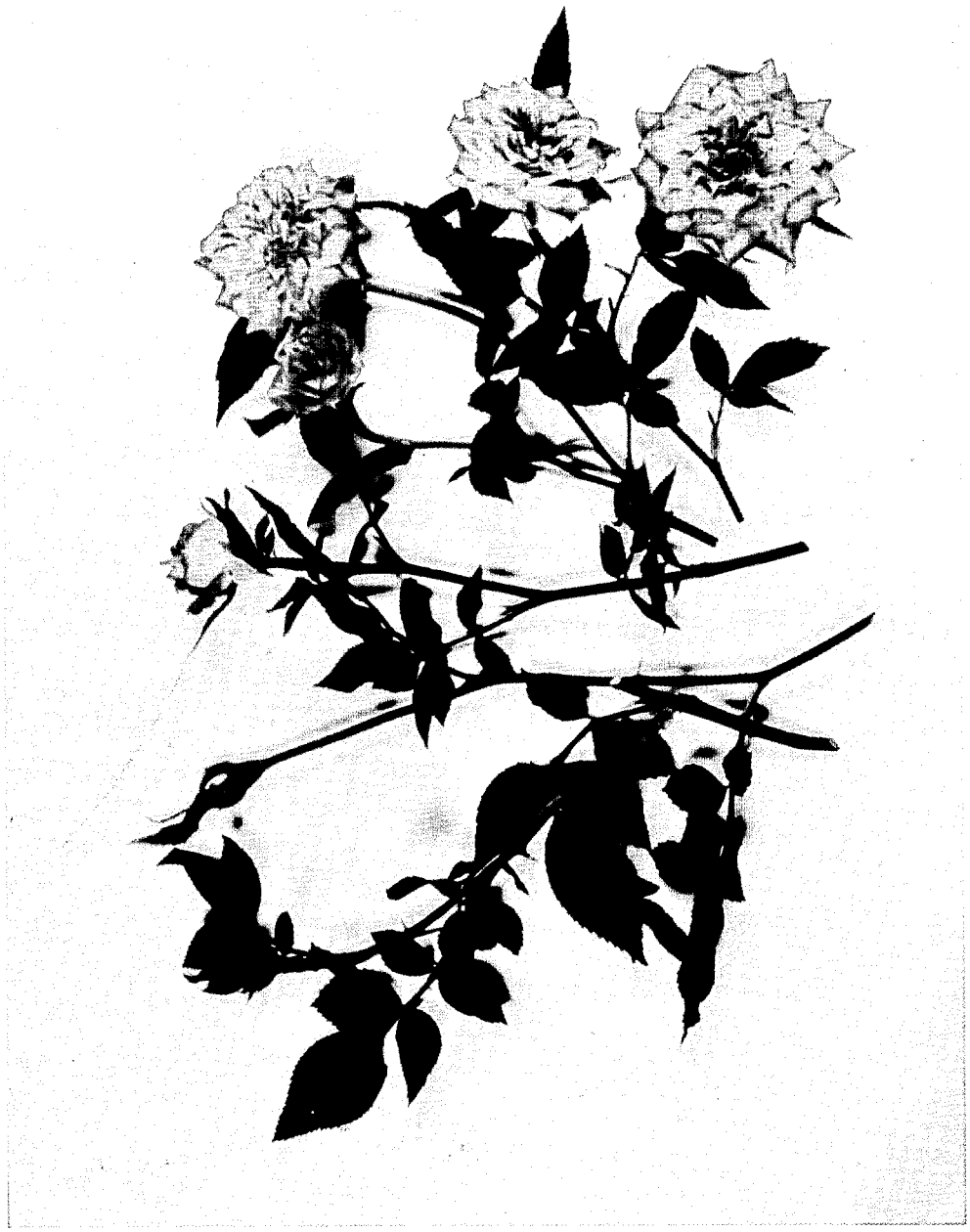

United States Patent

Plant Pat. 3,940

Patented Aug. 17, 1976

3,940

MINIATURE ROSE PLANT

Ralph S. Moore, 2519 E. Noble Ave., Visalia, Calif. 93277

Filed Aug. 18, 1975, Ser. No. 605,763

Int. Cl.[2] A01H 5/00

U.S. Cl. Plt.—9 1 Claim

The present invention relates to a new and distinct variety of hardy, dwarf, bush type rose plant of the miniature class; the variety being primarily characterized—as to novelty by deep pink to medium red buds and flowers which in general color effect are light to medium red when grown outdoors (deep pink to light red in plastic greenhouse).

The variety is further characterized by:

An abundance of bloom, with flowers borne singly or or several to stem in loose clusters.

Moderate fragrance.

A plant which is vigorous, of rounded upright shape, and with semi-glossy, small foliage with pointed leaflets; the flowers and foliage being similar in size to the variety Windy City (U.S. Plant Pat. No. 3,792). The plant has a normal average height of 12" to 14" at maturity can be easily maintained at lesser height by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Little Darling (a floribunda rose, U.S. Plant Pat. No. 1,581—expired) as the seed parent and Little Buckaroo (miniature—U.S. Plant Pat. No. 1,726) as the pollen parent.

Subsequent to origination of the variety I successfully asexually reproduced it in my nursery located as aforesaid, by budding as well as by cuttings; the reproductions having run true in all respects.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: hardy; dwarf; bush; seedling; greenhouse, outdoors; cut flowers; garden decoration; potted plant.

Class: Miniature.

Varietal name: Gypsy Jewel.

Flowers:

*Continuity.*—Continuous.

*Fragrance.*—Moderate.

Flowers borne: Singly and several together (3 to 5) on normal strength medium length stems.

Quantity of bloom: Abundant both outside and in greenhouse.

Bud:

*Peduncle.*—Medium length; slender; erect; medium green (usually tinted bronze, outdoors) very small short stiff hairs and sometimes some short prickles. Before calyx breaks, size—small. Form medium long; pointed with foliaceous appendages and numerous tiny short hairs on surface of the bud; with foliaceous parts extending beyond the tip of the bud equal to one-half or more of its length.

*Color.*—Medium green, usually tinted bronze (outdoors). As calyx breaks, color—red. As first petal opens: red, showing near-white at base of petal; size—small.

*Form.*—Medium length; pointed; becoming rounded or high centered. Opening—opens well in all weather.

Bloom:

*Size when fully open.*—Small, averaging 35–38 mm. (up to 1½").

*Petalage.*—Very double—up to 80 petals (plus several narrow petaloids) arranged regularly.

*Form.*—Slightly cupped at first, with petals rolled loosely outward, and later at maturity becoming high centered with petals being loosely rolled outward and with outer petals often rolled downward to give ball effect.

Petals: Thick; satiny both inside and outside. Shape—outside petals oval (broad lanceolate with acute tip); intermediate—broad lanceolate with acute tip; inside narrow lanceolate.

Color: Newly opened flower from a plant grown outdoors (June 1975), Visalia, Calif.

*Outside petal.*—Outside surface—near Rose Bengal 25 (with both lighter and darker areas) with white at base; inside surface—near Rose Red 724 with both lighter and darker areas and shading to near white at base.

*Intermediate petal.*—Outside surface—Rose Bengal 25 (with both lighter and darker areas) with white at base; inside surface—Rose Red 724 shading into near white at base.

*Inner petal.*—Outside surface—essentially same as intermediate petal but with more white area; inside surface—similar to intermediate petal but with proportionally more white area.

*General color effect newly opened flower.*—Light to medium red. Three days open—usually red color is deeper.

*Behavior.*—Spent petals usually hang on. Flower color is very lasting even in warm weather.

*Flower longevity (June 1975).*—Bush in garden or pot—5–7 days. Cut flowers at living room temperature—3 to 5 days.

Reproductive organs:

*Stamens.*—Very few—usually none.

*Filaments.*—Usually none.

*Pollen.*—None.

*Pistils.*—Few.

*Styles.*—Uneven; medium length; bunched; not well formed.

*Ovaries.*—All enclosed in calyx.

*Hips.*—None.

*Sepals.*—Permanent; spear shaped; recurved.

*Seeds.*—None.

Foliage:

*Leaves.*—Compound of five leaflets (sometimes 7); abundant; small to moderately small; leathery; semi-glossy to glossy.

*Leaflets.*—Shape: Lanceolate; apex acute; base rounded or rounded acute. Margin serrate. Color: Normal green; new growth often tinted bronze. Rachis: Medium strength; upper side slightly hairy, grooved, underside sparsely thorny. Stipules: Medium length; narrow; short to medium length points, turning out at an angle of 45 degrees or more.

Growth:

*Habit.*—Dwarf; bushy; rounded; much branched.

*Growth.*—Free; vigorous.

*Canes.*—Medium; slender.

*Main stems.*—Color: Dull green. Thorns: Moderately thorny; medium length; hooked slightly downward.

*Color.*—Medium brown. Prickles—none. Hairs—none.

*Branches.*—Color: medium green. Thorns: moderately thorny; short; hooked slightly downward; medium length oval base. Prickles—none. Hairs—none.

*New shoots.*—Color: Medium green, often tinted bronze. Thorns: Moderately thorny; short; hooked slightly downward; sharp; points; base oval. Prickles: Few to none.

The following is claimed:

1. A new and distinct variety of miniature rose plant of hardy dwarf, rounded, much branched, bush type as illustrated and described, characterized by buds and flowers resembling the Windy City (patent applied for) miniature rose in general form but color is more red rather than pink and flowers tend to open better, the general color effect being light to medium red; and further characterized by a plant which is of vigorous and compact growth, easy to propagate from cuttings, with medium small semi-glossy to glossy foliage and an abundancy of bloom, with flowers borne singly or several to stem in loose clusters.

No references cited.

ROBERT E. BAGWILL, Primary Examiner